United States Patent

Jürgens et al.

[11] Patent Number: 5,854,381
[45] Date of Patent: Dec. 29, 1998

[54] USE OF LACTIDE POLYMERS FOR ADHESION PROPHYLAXIS

[76] Inventors: Christian Jürgens; Hans Ryefger-Kricheldorf; Ingrid Kreiser-Saunders, all of c/o Merck KGaA 64271, Darmstadt, Germany

[21] Appl. No.: 775,885

[22] Filed: Jan. 2, 1997

[30] Foreign Application Priority Data

Jan. 3, 1996 [DE] Germany .................. 196 00 095.5

[51] Int. Cl.$^6$ .................................. C08G 63/08
[52] U.S. Cl. .................. 528/354; 528/310; 528/503; 424/443; 424/444; 525/419; 525/461
[58] Field of Search ................ 528/354, 310, 528/503; 424/443, 444; 525/461, 419

[56] References Cited

U.S. PATENT DOCUMENTS 5,206,341  4/1993  Ibay et al. .................. 528/361

*Primary Examiner*—Duc Truong
*Attorney, Agent, or Firm*—Millen, White, Zelano & Branigan, P.C.

[57] ABSTRACT

The invention relates to the use of absorbable physiologically acceptable sheets of copolymers for preventing postoperative adhesions after surgical procedures and is characterized in that the sheets consist of racemic lactide and $\epsilon$-caprolactone, $\sigma$-valerolactone, $\tau$-decalactone or $\beta$-hydroxybutyric acid, prepared by reacting the monomers in the molar ratio of lactide to partner in the reaction of from 90 to 70 30 to 10 with the addition of metal carboxylates which are known per se as initiator, with a ratio of partner in the reaction to initiator of from 300:1 to more than 1000:1 at temperatures of 130°–150° C. over a period of 24 to 96 hours.

12 Claims, No Drawings

USE OF LACTIDE POLYMERS FOR ADHESION PROPHYLAXIS

The invention relates to the use of physiologically acceptable sheets of copolymers for preventing postoperative adhesions after surgical procedures.

Postoperative adhesion is a pathological phenomenon. It is caused by surgical or accidental traumatization of tissue and is a uniting of connective tissues which results after sticking together by fibrin. Postoperative adhesions are complications which are frequently found clinically and which may occur after almost every surgical procedure. After a previous abdominal operation, 93 % of patients show adhesions, and most obstructions of the small bowel are caused by postoperative adhesions See D. Menzies et al., *Ann. Rev. R. Coll. Surg. Eng.,* 1990, 72:60; D. Menzies, *Surg. Ann.,* 1992, 24:27–45; and V. Schumpelick et al., *Chirurgie,* 3rd edition, 1994, Ferd. Enke Verlag, Stuttgart. The possibilities of the surgeon influencing this have been very small to date. Thus, it is scarcely possible to influence by surgical technique and drugs the development of bands (strands of connective tissue) and adhesions in cases of abdominal adhesions. See Schumpelick et al., supra. "Every abdominal procedure entails the risk of subsequent abdominal adhesions." V. Schumpelick et al., *Chirurgie,* 3rd edition, 1994, Ferd. Enke Verlag, Stuttgart.

The current state of the art can be summarized as follows:

The main method for adhesion prophylaxis is dissection of the traumatized tissue as cleanly as possible. Another point of attack is provided by fibrin, because previous sticking together with fibrin is the precondition for the formation of adhesions and bands of connective tissue. It is, therefore, attempted to prevent or break up sticking together by fibrin by flushing with physiological saline, especially the abdominal cavity after lengthy abdominal procedures, and by local use of fibrinolytics. However, these methods are not very successful because only part of the sticking together is ever affected.

In addition, various fabrics, lattices and sheets of absorbable copolymers of glycolide and lactide are employed in surgery. These are intended to facilitate or make possible healing processes, for example, in the case of damage to the spleen, or, after an amputation, keep organs in its direct vicinity in position, such as, for example, enclosure of the true pelvis towards the abdominal cavity after proctectomy See L. Röntgen et al., "Neue Hilfsmittel und Techniken in der Allgemeinchirurgie", in the series: *Praktische Chirurgie,* Vol. 104, 1994, Perd. Enke Verlag, Stuttgart). However, they are not employed to prevent adhesions. See L. Rontgen et al., supra) but occasionally in fact for deliberate scar formation, for example in inguinal hernia.

Among the plastics used in medicine, highly polymeric hydroxy carboxylic acid such as polylactide or polyglycolide occupy a special place. They have been employed in surgery for some time as absorbable sutures or osteosynthesis implants and as sheets for covering wounds. A material which can be used according to the invention and which has been described in German Patent 41 12 489 is distinguished by greater flexibility and adhesiveness compared with other wound-covering materials, such as those described in German Patent 36 20 685 or French Patent 2126270. This also applies to the thermoplastic copolymers which are disclosed in the patent WO 84/04331 and which are used as films or coatings for carbon fiber substrates used as implants in the body to heal damaged ligaments or tendons, and endoprostheses. However, these materials have likewise not been employed to date for adhesion prophylaxis.

Hence there is a need for a means for preventing postoperative adhesions.

It is now proposed according to the invention to use absorbable physiologically acceptable sheets of copolymers for preventing postoperative adhesions and bands after surgical procedures, the copolymers being prepared by reacting the monomers in the molar ratio of lactide to partner (monomeric compound) in the reaction of 90–70 to 30–10 with the addition of metal carboxylates which are known per se as initiator, with a ratio of partner in the reaction to initiator of from 300:1 to more than 1000:1 at temperatures of 130°–150° C. over a period of 24 to 96 hours. In addition, racemic glycolide can also be added to the reaction mixtures. The copolymers described in this way are suitable for topical use on a human or animal skin and resemble those already used for topical purposes, for example as incision sheet for operations, as sunscreen or insect repellant after addition of suitable active substances, as spray or sheet for covering wounds or as liquid glove. Further investigations, and practical applications, have surprisingly shown that these copolymers can be used to prevent postoperative adhesions in traumatized tissue. It has been assumed hitherto that adhesions would form through sheets, utilizing pores in the structure or that possibly even the formation of adhesions would be induced by polymers. It was all the more pleasing to find that the sheets form an effective barrier against the sticking together of the traumatized tissue as such and, where appropriate, the surrounding connective tissue by fibrin and, by reason of their physiological acceptability, lack of toxicity and absorbability, are outstandingly suitable therefor.

The copolymers used according to the invention are to be regarded on the basis of the chain length as poly- and oligomers and are in the form of a mixture of mono-, oligoand polymers. They are colorless transparent compounds which, depending on the molar ratio of the constituent monomers, are capable of viscous flow or are rigid. The claimed compounds are prepared by reacting the monomers in the molar ratio of lactide to partner in the reaction of 90 to 70:10 to 30, with an increase in the lactide content resulting in an increase in the softening temperature. In addition to the lactide and the partner in the reaction, racemic glycolide can also be reacted. The reaction takes place with the addition of metal carboxylates which are known per se as initiator at temperatures around 130°–150° C. for a period of 24 to 96 hours. The ratio of reaction mixture to initiator is 300:1 to 500:1, with an increase in this ratio in the reaction increasing the content of longer molecule chains and thus also causing an increase in the softening point. The initiator preferably employed is tin(II) diethylhexanoate because it has emerged that other initiators known per se afford a lower yield as a rule or lead to turbidity/coloring. In addition, a temperature of 130°–150° C. and a reaction time of 24 to 96 hours should not be exceeded. The reaction is stopped after the required reaction time either by cooling the reaction mixture or by adding, for example, chelating agents. To remove remaining monomers, short-chain oligomers or, where appropriate, also excess plasticizers, the reaction composition can, as a rule, be precipitated with 600 to 800 times the amount of alcohol; the reaction composition can also where appropriate be washed out with water or an aqueous solution because it is possible in this way also to remove a large part of the monomers, short-chain oligomers or plasticizers.

If required, plasticizers can be added to the reaction composition in order to alter the softening temperature and the diffusibility. Plasticizers which are preferably used are excess caprolactone, tributyl citrate, phthalic esters or glycerol. The plasticizer content should, as a rule, not exceed 10 to 20% based on weight. Glycerol has particular advantages as plasticizer because it has a certain bactericidal effect and increases the diffusibility of the sheets.

The copolymers according to the invention can be dissolved in suitable organic solvents such as, for example, ethyl acetate, acetone, methylene chloride or THF. They can be rolled without further additive to sheets which can, however, also be produced, for example, by evaporation. Other processing methods suitable for plastics can likewise be used.

Both the oligo- and the polymers are broken down by hydrolysis in vivo and in vitro. The copolymers and their breakdown products are medically innocuous and nonallergenic. The monomers are metabolized in vivo by the lactic acid cycle and by fatty acid metabolism. It has emerged that the times for hydrolytic breakdown decrease as the lactide content increases.

The use, claimed according to the invention, of sheets of the polymers described above is for covering traumatized tissue after a surgical procedure to prevent adhesions, it also being possible to add drugs, in particular antibiotics, to the sheet. Covering of the wound mechanically prevents unwanted sticking together of this and other connective tissues with fibrin during the healing process. This effectively precludes the formation of adhesions and bands simultaneously. The great advantage of the materials used according to the invention is that they can be broken down to innocuous products and thus no further surgical procedure is necessary to remove them, they can be easily applied and their detachability by aqueous fluids such as blood or lymph is low. In addition, the natural hydrolytic breakdown of the sheet in about 3 to 30 weeks in vitro provides the traumatized tissue with sufficient time for healing without the possibility of adhesions forming. The tear strength of copolymers of glycolide and lactide in vivo after 2 weeks is still more than 50%, and after 3 weeks is still 20%, of the original, and they are completely broken down in 75 days (see L. Röntgen et al., supra). The described sheets are particularly suitable, owing to their great mechanical strength and good adhesiveness, for tissues exposed to mechanical stimuli, such as muscles but also loops of bowel.

The invention is explained in detail hereinafter by means of the examples.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German DE 19600095.5 are hereby incorporated by reference.

EXAMPLES

Example 1
Production of a sheet from the copolymers

To produce a sheet from the copolymers, D,L-lactide (racemic lactide) and ε-caprolactone in a molar ratio of 85:15, corresponding to 350.5 grams to 49.0 grams, are slowly heated to 150° C. Then 1.16 ml of tin(II) diethylhexanoate (reaction composition:initiator ratio=500:1) are added as polymerization initiator. The polymerization takes place at 150° C. in an oil bath for 24 hours. The mixture is subsequently cooled and, at 70° C., made up to 5 liters with ethyl acetate. This solution then remains on a shaker for 36 hours and can then be used as such to produce sheets.

In a corresponding manner and taking account of the molar ratios, it is also possible to produce the copolymers of lactide, possibly with the addition of glycolide and the other lactones such as valerolactone, heptalactone, decalactone or else of β-hydroxybutyric acids.

Example 2
Use of a sheet for covering traumatized tissue after an invasive surgical procedure The sheet produced as in Example 1 is applied, before the end of a surgical procedure, to the traumatized tissues in such a way that they are completely covered. The surgical procedure is subsequently completed by closing the incision.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Physiologically acceptable sheets of copolymers for preventing postoperative adhesion after surgical procedures, wherein the copolymers are prepared by reacting racemic lactide and a monomeric compound selected from the group consisting of ε-caprolactone, σ-valerolactone, τ-decalactone and β-hydroxybutyric acid, in the molar ratio of lactide to monomeric compound of from 90 to 70:30 to 10 and wherein the reaction is carried out in the presence of tin-II-diethylhexanoate initiator in a ratio of total monomer in the reaction to initiator of from 300:1 to more than 1000:1 at a temperature of between 130°–150° C. over a period of 24 to 96 hours.

2. Physiologically acceptable sheets according to claim 1, wherein the copolymers are prepared by reacting racemic lactide, racemic glycolide and either ε-caprolactone or σ-valerolactone.

3. Physiologically acceptable sheets according to claim 1, which additionally contain one or more medicinally active substances.

4. Physiologically acceptable sheets according to claim 1, which additionally contain one or more physiologically acceptable plasticizers.

5. Physiologically acceptable sheets according to claim 3, which additionally contain antibiotics.

6. Physiologically acceptable sheets according to claim 4, which additionally contain glycerol.

7. A method of using an absorbable physiologically acceptable sheet of copolymers for preventing postoperative adhesions after surgical procedures which comprises applying said sheet to tissue, wherein the copolymers are prepared by reacting racemic lactide and a monomeric compound selected from the group consisting of ε-caprolactone, σ-valerolactone, τ-decalactone and β-hydroxybutyric acid, in the molar ratio of lactide to monomeric compound of from 90 to 70:30 to 10 with the addition of metal carboxylates as initiator, with a ratio of total monomer in the reaction to initiator of from 300:1 to more than 1000:1 at a temperature of between 130°–150° C. over a period of 24 to 96 hours.

8. A method according to claim 7, wherein the copolymers are prepared from racemic lactide, racemic glycolide and either ε-caprolactone or σ-valerolactone.

9. A method according to claim 7, where the sheets additionally contain one or more medicinally active substances.

10. A method of use according to claim 7, wherein the sheets additionally contain one or more physiologically acceptable plasticizers.

11. A method of use according to claim 9, wherein the sheets additionally contain antibiotics.

12. A method of use according to claim 10, wherein the sheets additionally contain glycerol.

* * * * *